Figure 1:
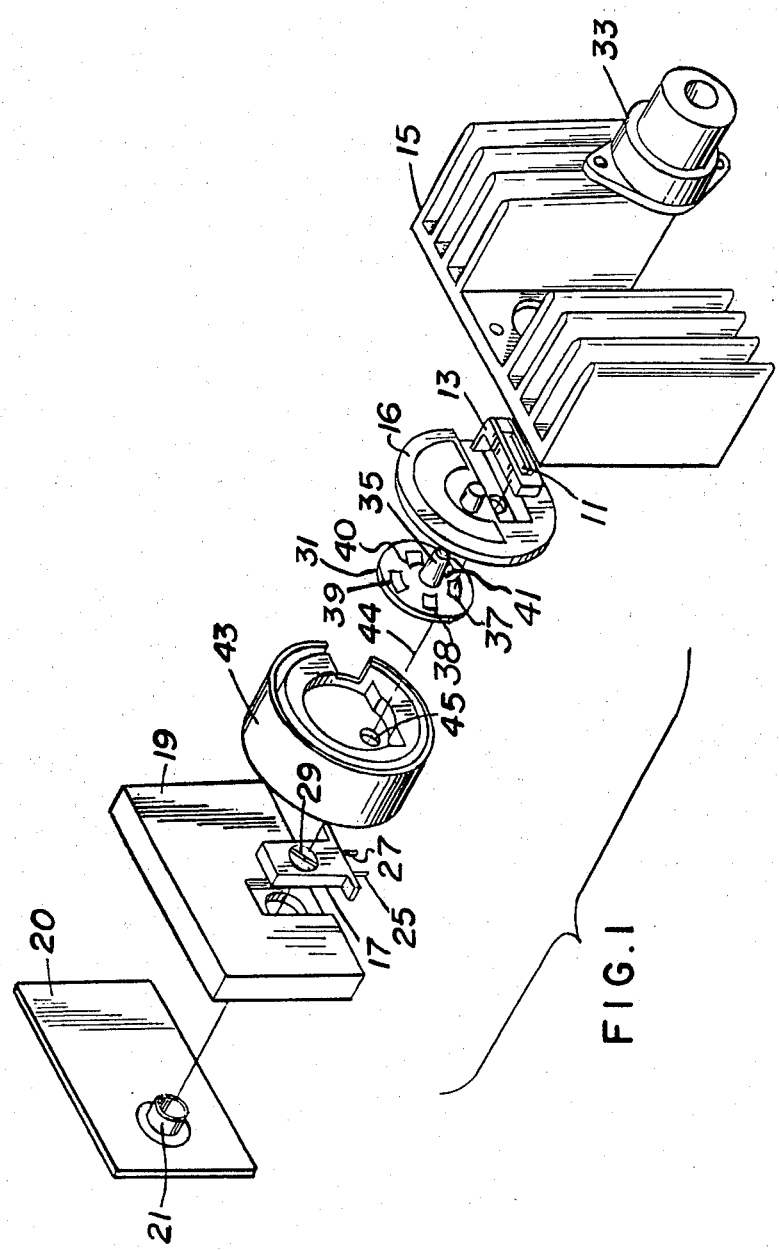

United States Patent [19]

Passaro et al.

[11] 4,423,739
[45] Jan. 3, 1984

[54] END TIDAL CARBON DIOXIDE GAS ANALYZER

[75] Inventors: Robert E. Passaro; Irvin G. Burough, both of Walnut Creek, Calif.

[73] Assignee: Andros Analyzers Incorporated, Oakland, Calif.

[21] Appl. No.: 295,486

[22] Filed: Aug. 24, 1981

[51] Int. Cl.³ .............................................. A61B 5/08
[52] U.S. Cl. .................................... 128/719; 128/633; 128/204.22; 250/345
[58] Field of Search ............... 128/719, 716, 633, 664, 128/204.22; 250/343–346

[56] References Cited

U.S. PATENT DOCUMENTS

| | | | |
|---|---|---|---|
| 3,790,797 | 2/1974 | Sternberg et al. | 250/345 |
| 3,893,770 | 7/1975 | Takami et al. | 250/345 X |
| 3,898,462 | 8/1975 | Ishida et al. | 250/344 |
| 3,953,734 | 4/1976 | Dimeff . | |
| 4,011,859 | 3/1977 | Frankenberger | 128/719 |
| 4,013,260 | 3/1977 | McClatchie et al. . | |
| 4,110,619 | 8/1978 | Zorner | 250/344 |
| 4,153,837 | 5/1979 | Ross | 250/346 X |
| 4,180,734 | 12/1979 | Gedean | 128/719 X |
| 4,281,248 | 7/1981 | Fabinski et al. | 250/343 X |

OTHER PUBLICATIONS

Nishi et al., Mass Spectroscopy, vol. 22, No. 3, Sep. 1974, pp. 191–198.
Puritan–Bennett/Datex "CO₂ Monitor & Recorder".

*Primary Examiner*—Kyle L. Howell
*Assistant Examiner*—John C. Hanley
*Attorney, Agent, or Firm*—Fitch, Even, Tabin & Flannery

[57] ABSTRACT

A method and apparatus are described for determining the partial pressure of carbon dioxide in the arterial blood of a patient. The method and apparatus are particularly useful where the patient is under anesthesia. Carbon dioxide concentration is measured at the end tidal of the patient's exhaled breath. Nitrous oxide concentration is also measured so that the measured values of the carbon dioxide concentration may be corrected in accordance with the measured value of the nitrous oxide concentration. Particular wavelengths of detection are described, together with other apparatus parameters to provide a high level of accuracy.

22 Claims, 2 Drawing Figures

END TIDAL CARBON DIOXIDE GAS ANALYZER

This invention relates generally to medical instrumentation and, more particularly, to a method and apparatus for determining the partial pressure of carbon dioxide in the arterial blood of a patient.

In numerous clinical settings, it becomes desirable to monitor the carbon dioxide concentration in the arterial blood of a patient under anesthesia. Invasive procedures have been designed for accomplishing this and include periodic sampling of arterial blood and the use of an in-dwelling catheter capable of directly monitoring the carbon dioxide concentration. The fact that such techniques are invasive subjects them to all the problems usually associated with such procedures, including the increased risk of infection, thrombosis, etc.

It is known that the carbon dioxide concentrations of the last gas expired from the lung (end tidal) in normal breathing is related to the carbon dioxide partial pressure in arterial blood gas. However, medical instruments designed to accomplish such monitoring have not been as accurate or as versatile as might be desired. Part of the difficulty arises from the fact that, in the operating room, nitrous oxide, which is commonly present in very high concentrations in the exhaled breath of a patient under anesthesia, can contribute substantial error to the carbon dioxide concentration measurement. In addition, respiratory rates can vary significantly between patients—from a typical rate of ten breaths per minute in a resting adult to up to 120 breaths per minute in neonates in respiratory distress. A further complication is that the volume of gas available from the patient's airway for analysis may be quite low—as little as 300 ml per minute.

It is an object of the present invention to provide an improved method and apparatus for determining the carbon dioxide concentration in the arterial blood of a patient.

Another object of the invention is to provide a method and apparatus for determining the end tidal concentration of carbon dioxide in the exhaled breath of a patient under anesthesia.

A further and more general object of the invention is to provide an improved gas analyzer capable of accurately measuring the carbon dioxide concentration of expired breath in the presence of high concentrations of nitrous oxide.

Figure 2:
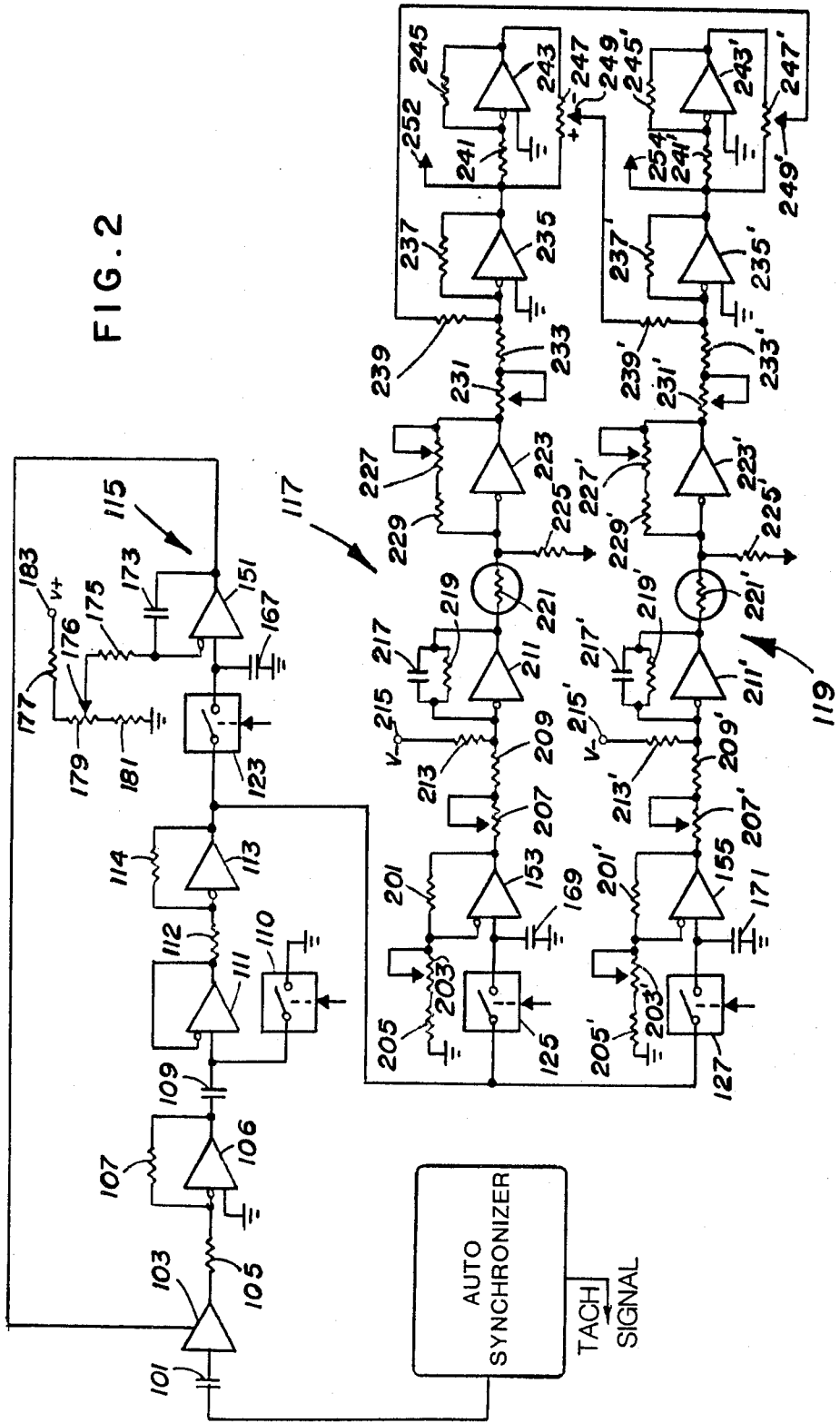

Other objects of the invention will become apparent to those skilled in the art from the following description, taken in conjunction with the accompanying drawings wherein:

FIG. 1 is a schematic partially exploded perspective view of apparatus constructed in accordance with the invention; and FIG. 2 is a schematic block diagram of the electronic portion of the apparatus of FIG. 1.

Very generally, the method and the apparatus of the invention determine the partial pressure of carbon dioxide in the arterial blood of a patient under anesthesia by detecting the carbon dioxide concentration at the end tidal of the patient's exhaled breath. The nitrous oxide concentration in the patient's breath is also detected and the detected values of the carbon dioxide concentration may be corrected in accordance with the detected value of the nitrous oxide concentration.

The apparatus of the invention is a nondispersive infrared gas analyzer which utilizes an infrared source to produce and direct infrared energy through an unknown gas mixture contained in a sample cell. Energy passing through the sample cell is detected and electrical signals are produced representative thereof. These signals are processed to produce an output indicating the concentration of one or more constituents of the gas in the sample cell.

Such gas analyzers utilize the principle that various gases exhibit substantially increased absorption characteristics at specific wavelengths in the infrared radiation spectrum. A gas analyzer of this type is shown and described in U.S. Pat. No. 4,013,260, McClatchie et al, issued Mar. 22, 1977, and assigned to the assignee of the present invention. Another type of nondispersive infrared gas analyzer is shown and described in U.S. Pat. No. 3,953,734, Dimeff, issued Apr. 27, 1976, and assigned to the United States of America.

In FIG. 1, the schematic perspective partially exploded view illustrates a nondispersive infrared gas analyzer. The gas analyzer includes an infrared source 11 of suitable design powered from a power supply, not shown. The source 11 is supported on a mounting bracket 13 which is mounted in thermal contact with a finned heat sink 15 by means of a circular mounting device 16. Infrared energy from the source 11 is transmitted through a gas sample cell 17 mounted on a support 19, to a detector 21 mounted on a support plate 20 and positioned in an opening 23 in the support 19. The detector 21 includes means (not shown) for maintaining it at a precise temperature. The sample cell 17 contains an inlet 25 and an outlet 27 for the exhaled breath of the patient, and windows 29 through which the infrared energy is transmitted. The patient's expired breath is conveyed to the inlet to the sample cell from the patient's airway by a suitable mask connection, not illustrated herein.

A rotary filter wheel 31 is positioned partially in the path of the infrared beam between the source and the sample cell. The filter wheel 31 includes a controller-drawer (not shown) to maintain it at a precise temperature and constant speed (RPM). The wheel 31 is rotated by a motor 33 through a drive shaft 35 to periodically interpose filters 37, 38 and 39 in the path of the infrared energy passing through the gas sample cell. The wheel 31 includes two additional positions 40 and 41 respectively termed a "spare" position and a "dark level" position. A housing 43 enclosed and supports the filter wheel 31 for rotation, and an opening 45 is provided in the housing 43 to permit the infrared energy to pass to the sample cell after passing through the filters. The optical path is shown by the dashed line 44.

One filter 37, called a reference filter, is selected to pass energy at a wavelength (nominally 3.690 microns, for example) at which none of the gases typically present in the exhaled breath of the patient will exhibit significant absorption. Accordingly, the light passing through the sample cell at this wavelength, which is a reference wavelength, can be used to determine attenuation of infrared energy resulting from factors other than absorption by the gas of interest. Such factors can include changes in the infrared energy output of the source, cloudiness of the windows of the sample cell, and degradation of the output of the detector. The bandwidth of the reference filter 37 is preferably narrow, for example, approximately 0.112 microns, to insure a channel which does not respond to any gases present in the cell. This channel serves as a monitor of the optical path "throughput" from the source through the detector to the preamp.

Another filter 38 in the filter wheel 31 is selected to pass energy at an absorption wavelength of carbon dioxide.

Typically a patient under anesthesia inhales a specially formulated atmosphere consisting of 20% oxygen, 1–4% anesthetic agent (such as halothane, ethrane, and penthane) 20–80% nitrous oxide, and the balance nitrogen. Accordingly, the expired gas in which the carbon dioxide concentration is to be measured contains a high concentration of nitrous oxide.

Such high concentrations of nitrous oxide can contribute to two sources of error in the measurement of carbon dioxide concentration. The first of these sources of errors, known as spectral interference, results from the fact that the infrared absorption spectrum of nitrous oxide contains a strong absorption band very close to the absorption band of the carbon dioxide filter. The second source of error is known as spectral line broadening and results from the fact that the carbon dioxide absorption spectra broadens in the presence of nitrous oxide and can result in an increased response of the analyzer to a typical gas mixture of $CO_2$ and $N_2O$.

In order to perform fast measurements of the amount of carbon dioxide in the small sample of breath using relatively inexpensive infrared sources and detector (such as lead selenide), an absorption band of carbon dioxide is used which is both a very strong absorber of radiation and which is also free of water vapor interference. The band at 4.25 $\mu$m will satisfy these requirements.

The reference filter 37 is located in a spectral region that is free of interference from other gases. In the apparatus of the present invention, the absorption band of the reference filter is located as close as possible to the absorption band of the carbon dioxide filter 38 to minimize instrument sensitivity to variations in source temperature. Such close proximity to the carbon dioxide wavelength reduces the effect of changes of source temperature on zero drift by a factor of 3.

In addition to the reference filter 37 and the carbon dioxide filter 38, the apparatus of the present invention incorporates an additional filter 39 in the optical path which is used to determine the nitrous oxide concentration in the sample. Accordingly, with a determination of nitrous oxide concentration, the effect of spectral line broadening error in the carbon dioxide measurement in the presence of nitrous oxide can be corrected for by utilizing the measured nitrous oxide concentration in a suitable correction formula. For example, a formula as follows will provide for correction for nitrous oxide concentration:

$$C_C = C_M(1 + KC_{N_2O})$$

where: $C_C$ = corrected $CO_2$ concentration, $C_M$ = measured $CO_2$ concentration, $C_{N_2O}$ = measured $N_2O$ concentration, and K = a spectral line broadening constant which may be empirically determined.

In selecting the absorption band of the nitrous oxide filter 39, there are four absorption bands of nitrous oxide that are free of interference from other gases typically used in anesthesia and which are therefore present in exhaled breath of an anesthetized patient. Such bands are located at 3.6, 3.9, 4.08 and 4.55 $\mu$m, respectively. The band at 4.55 $\mu$m absorbs almost all of the radiation at concentrations of nitrous oxide of the type typically present in the exhaled breath of a patient under anesthesia. The 3.6 and 4.07 $\mu$m bands absorb less than a few parcent of radiation. Only the band at 3.9 $\mu$m will absorb sufficient radiation (8% of the pulse) to be usable for measuring nitrous oxide in the sampled gas. Thus, the filter 39 used to measure the nitrous oxide in the present invention is located at 3.875 microns with a bandwidth of approximately 0.155 microns. In accordance with the preceding discussion, this wavelength is chosen so there is no significant absorption from gases in the cell other than nitrous oxide.

The spare position 40 is provided to permit detection of an additional gas. The dark level position 41 is a blank portion of the filter wheel which serves as a reference of absolute radiation. The filter wheel 31 is preferably temperature controlled to provide this absolute radiation reference level.

In order to cope with respiratory rates ranging from 10 breaths per minute to 120 breaths per minute, a fast response time is required in the apparatus of the invention. Moreover, typical gas flow rate available from the airway of a patient may be as little as 50 ml per minute. To accomodate such factors, the present invention utilizes a response time of 150 milliseconds or less. To this end, a very small gas sample cell is used, having a volume less than about 25 $\mu$l and preferably approximately 20 $\mu$l. At a flow rate of 50 ml per minute, a 20 $\mu$l sample cell is flushed in 24 milliseconds. Theoretically, the pneumatic response time 10–90% occurs in 2.3 flush times or a total time of 55 milliseconds. By designing the electronics with a response time of about 50 milliseconds, a total response time of just over 100 milliseconds is achieved, well within the desired time.

The apparatus of the invention is typically coupled to the patient's airway through a sampling catheter which consists of about 3–8 feet of 0.040 inch diameter tubing. Some degradation of an abrupt change in gas concentration at the inlet of the catheter always occurs as the concentration gradient proceeds to the apparatus. All of these contributions to response time combine to yield an overall response time of less than 150 milliseconds, at a flow rate of 50 ml per minute.

Referring now to FIG. 2, a schematic block diagram illustrating the function of the signal processing circuitry of the invention is shown. Signals from the detector output are applied through a capacitor 101 to an AGC amplifier 105. The output of the amplifier 103 is applied through a resistor 105 to the negative input of a preamplifier 106. The positive input is grounded and a feedback resistor 107 is connected from the output of the amplifier 103 to its negative input. The output of the preamplifier is applied through a capacitor 109 to the positive input of an amplifier 111. The negative input of the amplifier 111 is coupled to the amplifier output. A dark level switch 110 clamps the amplifier's positive input to ground during periods when the infrared beam is blocked, as is known in the art.

The output of the amplifier 111 is applied through a resistor 112 to a further amplifier 113 at the negative input thereof. A feedback resistor 114 connects the output of the amplifier 113 to its negative input.

The output of the detector 21, after amplification in the preamplifier 103 and the automatic gain control amplifier 111, is applied sequentially to three different channels, namely, the reference channel 115, the carbon dioxide channel 117, and the nitrous oxide channel 119. Sequential application at the proper time is provided through analog switches 123, 125 and 127, respectively, which are controlled to close at appropriate times corresponding to the particular filter which is interposed in the path of the infrared energy. Additionally, the switch 110 is similarly controlled to close when the infrared energy is blocked.

Timing signals are generated by applying the output signals of the detector to an autosynchronizer 131. The autosynchronizer 131 provides output signals to the dark level or clamping switch 110, the reference channel switch 123, the carbon dioxide channel switch 125 and the nitrous oxide channel switch 127. It should be noted at this point that an additional channel or channels may be provided as desired identical to the carbon dioxide and nitrous oxide channels described below if additional gases are to be monitored. In such a case, the autosynchronizer may be adapted to provide additional synchronizing signals as necessary. The autosynchronizer may be of any suitable design but preferably is constructed in accordance with that shown and described in the U.S. Pat. No. 4,241,309.

Each of the three channels 115, 117 and 119 is provided with an amplifier 151, 153 and 155, respectively, through which the signal from the analog switch is applied. A capacitor 167, 169 and 171, respectively, connects the positive inputs of the amplifiers in each channel to ground.

The amplifier 151 is provided with a feedback resistor 173 which is connected to the variable tap 176 of a voltage divider network through a resistor 175. The voltage divider network includes series resistors 177, 179 and 181 connecting a source 183 of positive potential to ground. Variation of the tap 176 controls the composite gain of the channel 115, the output of which is connected back to the automatic gain control amplifier 103. By properly setting the variable tap 176, during the reference signal interval, the gain of the system will be adjusted in accordance with the desired reference level as is known in the art of infrared gas analyzers.

The carbon dioxide channel 117 and the nitrous oxide channel 119 are identical. Accordingly, further detailed description will be given only in connection with the carbon dioxide channel 117. Components in the nitrous oxide channel 119 having similar functions to those in the channel 117 have been given identical reference numbers and have been primed.

The amplifier 153 in the carbon dioxide channel 117 is provided with a coarse zeroing circuit including a resistor 201 connecting the output of the amplifier 153 to the biasing input thereof. The resistor 201 is also connected through a variable pot 203 and a fixed resistor 205 to ground. Setting of the variable pot 203 adjusts the output level of the amplifier 153 to the desired level for accurate operation and may be preset at the factory during manufacture.

The output of the amplifier 153 is applied through a variable pot 207 and a fixed resistor 209 to the negative input of an amplifier 211. The positive input of the amplifier 211 is grounded and the negative input is connected through a fixed resistor 213 to a source of negative potential 215. A bandwidth limiting feedback network comprising the parallel combination of a capacitor 217 and resistor 219 is connected from the output of the amplifier 211 to the negative input thereof. Variation in the pot 207 adjusts the output of the channel to the desired calibration level.

When no carbon dioxide is present in the sample cell, the output of the amplifier 211 is nominally a zero and the output of the amplifier 153 is set at a nominal level, for example, 5 volts. If this output is 5 volts when no carbon dioxide is present, the introduction of a given level of carbon dioxide concentration in the sample cell causes the output voltage of the amplifier 153 to change a corresponding amount. Anomalies in the electro-optical system of the gas analyzer may cause the output voltage of the amplifier 153 to drift over a period of time. For example, if the output voltage of the amplifier drifts to a point where the output level is 4 volts when no carbon dioxide is present (and with the output of the amplifier 211 set at zero), the presence of a given level of carbon dioxide in the sample cell will change the output of the amplifier. To insure that the percentage change under the circumstances is the same as that when the nominal output is 5 volts, the circuit is designed to avoid span error.

The variable pot 207, together with the circuitry associated with the amplifiers 153 and 211, compensates for the possibility of span error. Adjustment of the variable resistor 207 is made to bring the nominal output voltage of the amplifier 211 to a zero output. The percent change in that output resulting from the presence of carbon dioxide in the sample cell will be the same regardless of the actual voltage at the output of the amplifier 153. Accordingly, the system is span-stabilized.

The output of the amplifier 211 is applied through a thermistor 221 which compensates the system for variations in ambient temperature, particularly of the gas in the sample cell which can result in a variation in the gas absorption. The thermistor 221 passes the output signal from the amplifier 211 to the negative input of an amplifier 223. The positive input of the amplifier 223 is grounded and a bias resistor 225 connects the negative input to ground. The output of the amplifier 223 is connected through a variable pot 227 and a fixed resistor 229 to its negative input to provide for coarse adjustment of the span characteristics of the channel. Adjustment of the coarse span in the presence of a suitable calibrating gas in the sample cell may be made at the factory. Fine adjustment is provided for by a series pot 231 connected to the output of the amplifier 223 and controllable from the control panel of the apparatus, not shown.

The variable pot 231 is series connected with a fixed resistor 233 to the negative input of an amplifier 235. The positive input of the amplifier 235 is grounded and a feedback resistor 237 is connected from the output of the amplifier 235 to its negative input. The amplifier 235 is for summing in a cross-talk signal which is applied thereto from the nitrous oxide channel 119 through a resistor 239. The output of the amplifier 235 at the terminal 252 represents the carbon dioxide signal which measures the concentration of the carbon dioxide in the sample cell.

To provide for cross-talk compensation in the nitrous oxide channel, the output of the amplifier 235 is also applied, through a resistor 241 to the negative input of a unity gain inverting amplifier 243. The positive input of the amplifier 243 is grounded and a feedback resistor 245 connects the output of the amplifier 243 with the negative input thereof. The output of the amplifier 243 is applied to a pot 247 which has a variable tap 249 thereon. Adjustment of the variable tap 249 at the factory to the desired level is made to minimize cross-talk between the channels.

In operation, the illustrated apparatus provides a continuous output signal on each channel 117 and 119 at the terminals 252 and 254, respectively. Although the signal at the terminal 254 representing N₂O will remain substantially constant throughout the patient's breath cycle, the CO₂ reading at the terminal 252 will vary. Typically this reaches a peak at the end tidal of the patient's breath and it is this portion of the signal which is used for further processing as described previously.

It may be seen, therefore, that the invention provides an improved method and apparatus for determining the partial pressure of carbon dioxide in the arterial blood of a patient under anesthesia. The invention constitutes a non-invasive procedure by which the carbon dioxide concentration at the end tidal of the patient's expired breath is accurately and quickly measured. Means are provided for maximizing the signal to noise ratio and reducing the response time of the system to very low levels. An improved arrangement for span stabilization is also provided.

Various modifications of the invention will become apparent to those skilled in the art from the foregoing description and accompanying drawings. Such modifications are intended to fall within the scope of the appended claims.

What is claimed is:

1. A method for determining the partial pressure of carbon dioxide in the arterial blood of a patient under anesthesia, comprising, detecting the carbon dioxide concentration at the end tidal of the patient's exhaled breath by measuring the infrared energy absorbed at a predetermined first wavelength band coinciding with a peak absorption wavelength of carbon dioxide, detecting the nitrous oxide concentration at the end tidal of the patient's exhaled breath by measuring the infrared energy absorbed at a predetermined second wavelength band coinciding with a peak absorption wavelength of nitrous oxide, and correcting the detected value of the carbon dioxide concentration in accordance with the detected value of the nitrous oxide concentration.

2. A method according to claim 1 wherein the measurements are made on breath by breath basis.

3. A method according to claim 1 wherein the carbon dioxide concentration detected value is corrected by multiplying by one plus the product of a constant times detected value of the nitrous oxide concentration.

4. A method according to claim 1 wherein the carbon dioxide concentration is detected by measuring infrared absorption of carbon dioxide at a nominal wavelength of about 4.7 μm and wherein the nitrous oxide concentration is detected by measuring infrared absorption of nitrous oxide at a nominal wavelength of about 3.9 μm.

5. A method according to claim 4 wherein such measurements are referenced to the infrared absorption at a nominal wavelength of about 3.75 μm.

6. A method according to claim 4 wherein the bandwidths at the nominal carbon dioxide wavelength and the nitrous oxide wavelength are less than about 0.1 μm.

7. A method according to claim 5 wherein the bandwidths at the nominal referenced wavelength is less than about 0.12 μm.

8. Apparatus for determining the partial pressure of carbon dioxide in the arterial blood of a patient under anesthesia, comprising, means for detecting the carbon dioxide concentration at the end tidal of the patient's exhaled breath by measuring the infrared energy absorbed at a predetermined first wavelength band coinciding with a peak absorption wavelength of carbon dioxide and for producing a signal proportional thereto, means for detecting the nitrous oxide concentration at the end tidal of the patient's exhaled breath by measuring the infrared energy absorbed at a predetermined second wavelength band coinciding with a peak absorption wavelength of nitrous oxide and for producing a signal proportional thereto, and means for correcting the detected value of the carbon dioxide concentration in accordance with the detected nitrous oxide concentration.

9. Apparatus according to claim 8 wherein said detecting means include a sample cell for holding the patient's exhaled breath, means for passing a beam of infrared radiation through said sample cell, and means for detecting the absorption of the infrared radiation passing through the sample cell at wavelengths whereat such infrared radiation is absorbed by carbon dioxide and by nitrous oxide, respectively.

10. Apparatus according to claim 9 including filter means providing for measurement of infrared absorption by carbon dioxide at a nominal wavelength of 4.2 μm, and providing for measurement of absorption by nitrous oxide at a nominal wavelength of 3.9 μm.

11. Apparatus according to claim 10 further including reference filter means for measurement of infrared absorption at a reference nominal wavelength of 3.75 μm.

12. Apparatus according to claim 11 wherein the bandwidths of said filter means for carbon dioxide and nitrous oxide are less than about 0.1, and wherein the bandwidths for the reference filter is less than 0.12.

13. Apparatus according to claim 9 wherein the volume of said sample cell is less than about 25 μl.

14. Apparatus according to claim 11 including means for span normalization of the carbon dioxide concentration output signal.

15. Apparatus according to claim 14 wherein said normalization means includes amplifier means, first variable resistance means connected in a feedback configuration from the output of said amplifier means to the input thereof for coarse adjustment, and second variable resistance means connected in series with the output of said amplifier means for fine adjustment.

16. Apparatus for detecting the carbon dioxide concentration at the end tidal of a patient's exhaled breath in the presence of nitrous oxide, comprising a sample cell for containing the patient's exhaled breath, means for passing a beam of infrared radiation through said sample cell, means for measuring the infrared energy absorbed at a predetermined first wavelength band coinciding with a peak absorption wavelength of carbon dioxide, and means for measuring the infrared energy absorbed at a predetermined second wavelength band coinciding with a head absorption wavelength of nitrous oxide, whereby the measured value of the infrared energy absorbed at said first wavelength band when corrected in accordance with the measured value of the infrared energy absorbed at said second wavelength band provides an accurate measure of carbon dioxide concentration.

17. Apparatus according to claim 16 including filter means providing for measurement of infrared absorption by carbon dioxide at a nominal wavelength of 4.2 μm, and providing for measurement of absorption by nitrous oxide at a nominal wavelength of 3.9 μm.

18. Apparatus according to claim 17 further including reference filter means for measurement of infrared absorption at a reference nominal wavelength of 3.75 μm.

19. Apparatus according to claim 18 wherein the bandwidths of said filter means for carbon dioxide and nitrous oxide are less than about 0.1, and wherein the bandwidths for the reference filter is less than 0.12.

20. Apparatus according to claim 16 wherein the volume of said sample cell is less than about 25 $\mu l$.

21. Apparatus according to claim 18 including means for span normalization of the carbon dioxide concentration output signal.

22. Apparatus according to claim 21 wherein said normalization means includes amplifier means, first variable resistance means connected in a feedback configuration from the output of said amplifier means to the input thereof for coarse adjustment, and second variable resistance means connected in series with the output of said amplifier means for fine adjustment.

* * * * *

UNITED STATES PATENT AND TRADEMARK OFFICE
CERTIFICATE OF CORRECTION

PATENT NO. : 4,423,739

DATED : January 3, 1984

INVENTOR(S) : Robert E. Passaro, and Irvin G. Burough

It is certified that error appears in the above-identified patent and that said Letters Patent is hereby corrected as shown below:

Column 2, line 47, change "enclosed" to --encloses--.

Column 4, line 2, change "parcent" to --percent--.

Column 4, line 22, change "accomodate" to --accommodate--.

Column 4, line 47, change "amplifier 105" to --amplifier 103--.

Column 8, line 52, change "head" to --peak--.

Signed and Sealed this

Eleventh Day of September 1984

[SEAL]

Attest:

Attesting Officer

GERALD J. MOSSINGHOFF

Commissioner of Patents and Trademarks